(12) United States Patent
Young et al.

(10) Patent No.: US 6,680,342 B2
(45) Date of Patent: Jan. 20, 2004

(54) METHODS AND COMPOSITIONS FOR INHIBITING THE PROLIFERATION OF PROSTATE CANCER CELLS

(75) Inventors: Charles Young, Rochester, MN (US); Nianzeng Xing, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 77 days.

(21) Appl. No.: 09/957,359

(22) Filed: Sep. 20, 2001

(65) Prior Publication Data

US 2003/0054357 A1 Mar. 20, 2003

(51) Int. Cl.$^7$ .............................................. A61K 31/19
(52) U.S. Cl. ...................................................... 514/557
(58) Field of Search ........................................ 514/557

(56) References Cited

U.S. PATENT DOCUMENTS 5,763,415 A * 6/1998 Sukumar
6,426,362 B1 * 7/2002 Miller et al.

OTHER PUBLICATIONS

Baker et al, Proc. Soc. Bio. Med., vol. 217(3), pp. 317–321 (abstract) Mar. 1998.*
Knowles et al, Nutr. Cancer, vol. 38(1), pp. 116–122 (abstract) 2000.*
Kampa et al, Nutr. Cancer, vol. 37(2), pp. 223–233 (abstract) 2000.*
Xing et al, Carcinogenesis, vol. 22(3), pp. 409–414 (abstract) Mar. 2001.*
Csokay et al., "Molecular Mechanisms in the Antiproliferative Action of Quercetin," *Life Sciences*, 1997, 60(24):2157–2163.
Culig et al., "Expression, Structure, and Function of Androgen Receptor in Advanced Prostatic Carcinoma," *The Prostate*, 1998, 35:63–70.
Deschner et al., "Quercetin and rutin as inhibitors of azoxymethanol–induced colonic neoplasia," *Carcinogenesis*, 1991, 12(7):1193–1196.
Ellattar and Virji, "The Effect of Red Wine and its Components on Growth and Proliferation of Human Oral Squamous Carcinoma Cells," *Anticancer Res.*, 1999, 19:5407–5414.
Le Marchand et al., "Intake of Flavonoids and Lung Cancer," *J. Natl. Cancer Inst.*, 2000, 92(2):154–160.
Miodini et al., "The two phyto–oestrogens genistein and quercetin exert different effects on oestrogen receptor function," *Br. J. Cancer*, 1999, 80(8):1150–1155.
Mitchell et al., "Resveratrol Inhibits the Expression and Function of the Androgen Receptor in LNCaP Prostate Cancer Cells," *Cancer Research*, 1999, 59:5892–5895.
Plaumann et al., "Flavonoids activate wild–type p53," *Oncogene*, 1996, 13:1605–1614.
Ren et al., "Tea polyphenols down–regulate the expression of the androgen receptor in LNCaP prostate cancer cells," *Oncogene*, 2000, 19:1924–1932.
Richter et al., "Quercetin–Induced Apoptosis in Colorectal Tumor Cells: Possible Role of EGF Receptor Signaling," *Nutrition and Cancer*, 1999, 34:88–99.
Stavric, "Quercetin in Our Diet: From Potent Mutagen to Probable Anticarcinogen," *Clin. Biochem.*, 1994, 27(4):245–248.
Yoshida et al., "Quercetin Arrests Human Leukemic T–Cells in Late $G_1$ Phase of the Cell Cycle," *Cancer Research*, 1992, 52:6676–6681.
Zhu et al., "A Nonsteroidal Anti–inflammatory Drug, Flufenamic Acid, Inhibits the Expression of the Androgen Receptor in LNCaP cells," *Endocrinology*, 1999, 140(11):5451–5454.

* cited by examiner

*Primary Examiner*—James H. Reamer
(74) *Attorney, Agent, or Firm*—Fish & Richardson P.C., P.A.

(57) ABSTRACT

The invention provides for methods of monitoring the proliferation of cultured prostate cancer cells in the presence of quercetin, methods of treating an individual with prostate cancer or at risk of developing prostate cancer, and methods of reducing the risk of recurrence of prostate cancer in an individual who had previously been treated for prostate cancer. Methods of the invention further include treating an individual with benign prostatic hyperplasia (BPH) with quercetin as well as methods of screening for compounds that inhibit the proliferation of prostate cancer cells. The invention provides for compositions and articles of manufacture containing quercetin in particular formulations, and quercetin with a second compound that also exerts an effect on the androgen receptor.

21 Claims, 5 Drawing Sheets

METHODS AND COMPOSITIONS FOR INHIBITING THE PROLIFERATION OF PROSTATE CANCER CELLS

FEDERALLY SPONSORED RESEARCH OR DEVELOPMENT

The U.S. Government may have certain rights in this invention pursuant to NIH grants DK41995 and CA 70892.

TECHNICAL FIELD

This invention relates to prostate cancer, and more particularly to methods and compositions for inhibiting the proliferation of prostate cancer cells.

BACKGROUND

The prostate gland is located between the bladder and the rectum and wraps around the urethra. The prostate is composed of glandular tissue that produces a milky fluid and smooth muscles that contract during sex and squeeze this fluid into the urethra where it mixes with other fluid and sperm to form semen. The prostate gland converts testosterone to a more powerful male hormone, dihydrotestosterone, which affects the size of the gland and plays an important role in prostate cancer.

Prostate cancer is a malignant tumor that arises in the prostate gland and can eventually spread through the blood and lymph fluid to other organs, bones, and tissues. Prostate cancer is the most commonly diagnosed cancer in the U.S., and it is the second leading cause of cancer death in American men after non-melanoma skin cancer. Although prostate cancer is just as common in Japan as in the United States, death rates from prostate cancer are significantly lower in Japan. It is unlikely that these differences are all genetic, because Japanese men who migrate to the United States die of prostate cancer with increasing frequency as a function of the number of years they reside in the United States. It is possible that this paradox could be explained, at least in part, by dietary factors.

Benign prostatic hyperplasia (BPH) is a benign enlargement of the prostate gland caused by the growth of both glandular and stromal tissues. Because the prostate enlargement in BPH is affected by testosterone, many men are concerned that it may be related to prostate cancer. A ten-year study, however, found no higher risk for prostate cancer in men with or that have experienced BPH. BPH develops in the inner zone of the prostate (i.e., predominantly stromal cells), while cancer tends to develop in the outer area (i.e., epidermal cells).

SUMMARY

It is reported herein that the expression of the androgen receptor was inhibited by quercetin. Accordingly, the invention provides for methods of monitoring the proliferation of cultured prostate cancer cells in the presence of quercetin, methods of treating an individual with prostate cancer or at risk of developing prostate cancer, and methods of reducing the risk of recurrence of prostate cancer in an individual who had previously been treated for prostate cancer. Methods of the invention further include treating an individual with benign prostatic hyperplasia (BPH) as well as methods of screening for compounds that inhibit the proliferation of prostate cancer cells. The invention provides for compositions and articles of manufacture containing quercetin in particular formulations, or quercetin with a second compound that also exerts an effect on the androgen receptor.

In one aspect, the invention provides methods of monitoring the proliferation of cultured prostate cancer cells in the presence of quercetin. Such a method includes contacting cultured prostate cancer cells with quercetin, and determining the level of expression of a gene encoding an androgen receptor. Generally, a decrease in androgen receptor expression in the prostate cancer cells indicates an inhibitory effect by quercetin on the proliferation of the prostate cancer cells. Representative prostate cancer cell lines include LNCaP cells or LAPC-4 cells.

In another aspect, the invention provides methods of treating an individual with prostate cancer or at risk of developing prostate cancer. Methods of treating an individual with prostate cancer or at risk of developing prostate cancer include identifying an individual with prostate cancer or at risk of developing prostate cancer, and administering a dose of quercetin to the individual that is effective to inhibit expression of a gene encoding an androgen receptor. The method also can include monitoring expression of the gene encoding the androgen receptor in the individual. Decreasing androgen receptor expression inhibits the proliferation of prostate cancer cells, thereby treating the individual. For example, quercetin can be administered to a human, and in an amount of from about 50 mg/kg to about 1000 mg/kg. Quercetin can be administered orally, transdermally, intravenously, intraperitoneally, or using an implant.

In still another aspect, the invention provides for methods of reducing the risk of recurrence of prostate cancer in an individual who previously had been treated for prostate cancer. Such a method includes the step of administering a dose of quercetin to the individual that is effective to inhibit expression of a gene encoding an androgen receptor. The method can further include the step of monitoring expression of the gene encoding the androgen receptor in the individual. Generally, decreasing androgen receptor expression inhibits the proliferation of prostate cancer cells, thereby reducing the risk of recurrence of prostate cancer in the individual. The individual may have previously undergone a radical prostectomy.

In yet another aspect, the invention provides methods of treating an individual with benign prostatic hyperplasia (BPH). This method includes identifying an individual with BPH, and administering a dose of quercetin to the individual that is effective to inhibit expression of a gene encoding an androgen receptor. The method also can include monitoring expression of the gene encoding the androgen receptor in the individual. Inhibiting the expression of a gene encoding an androgen receptor thereby treating the BPH in the individual.

The invention additionally provides methods of screening for compounds that inhibit the proliferation of prostate cancer cells, including contacting prostate cancer cells with a compound, and determining the transactivating ability of an androgen receptor. The method also can include monitoring the transactivating ability of the androgen receptor in the prostate cancer cells. Decreased transactivating ability of the androgen receptor in the prostate cancer cells compared to prostate cancer cells not contacted with the compound indicates a compound that inhibits the proliferation of prostate cancer cells.

The invention additionally provides methods of screening for compounds that inhibit the proliferation of prostate cancer cells, including contacting prostate cancer cells with a compound, and determining the level of expression of a gene encoding an androgen receptor. The method also can include monitoring expression of the gene encoding the androgen receptor in the prostate cancer cells. Decreased androgen receptor expression in the prostate cancer cells compared to prostate cancer cells not contacted with the compound indicates a compound that inhibits the proliferation of prostate cancer cells. Prostate cancer cells such as LNCaP cells or LAPC-4 cells can be used in this method.

Further, the invention provides compositions that include quercetin, one or more compounds that have a particular mechanism of action (i.e., inhibiting expression of a gene encoding an androgen receptor, inhibiting nuclear localization of an androgen receptor, and inhibiting the transactivating ability of an androgen receptor) and a pharmaceutically acceptable carrier. Representative examples of compounds having particular mechanisms of action include silymarin, silibin, docosahexaenoic acid (DHA), eicosapentaenoic acid (EPA), perillyl alcohol (POH) or a derivative thereof, resveratrol, flufenamic acid, tea polyphenols, and anti-androgen compounds. It is a feature of the invention to provide such a composition in the form of an article of manufacture (e.g., a kit). Such an article of manufacture can include packaging material comprises instructions for using the composition to inhibit the expression of a gene encoding an androgen receptor in an individual.

In another aspect of the invention, there are provided compositions that include quercetin and that are formulated for transdermal delivery to the prostate of an individual. Delivery to the prostate typically inhibits expression of a gene encoding an androgen receptor. In addition, the invention provides compositions that include quercetin and that are formulated for implantation near the prostate of an individual. Generally, implantation near the prostate inhibits expression of a gene encoding an androgen receptor.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

Figure 1A:
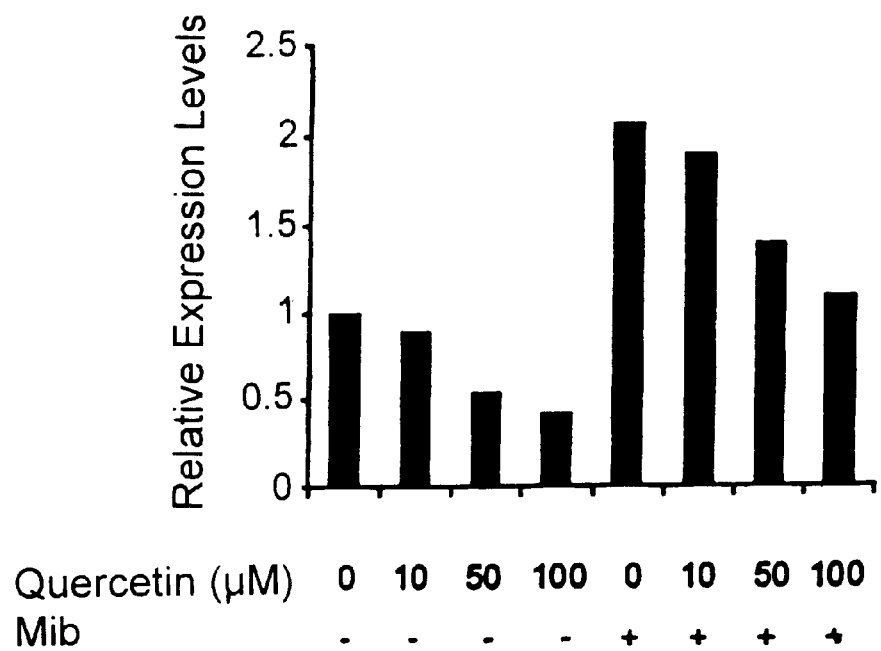
FIG. 1 shows an analysis of androgen receptor expression levels in the presence of quercetinin in whole cell lysates (FIG. 1A) or nuclear extracts (FIG. 1B) from LNCaP cells, or whole cell lysates from LAPC-4 cells (FIG. 1D).
FIG. 1C shows the expression levels of Sp1 in the presence and absence of quercetin.

It is reported herein that expression of the androgen receptor was inhibited by quercetin. Accordingly, the invention provides for methods of monitoring the proliferation of cultured prostate cancer cells in the presence of quercetin, methods of treating an individual with prostate cancer or at risk of developing prostate cancer, and methods of reducing the risk of recurrence of prostate cancer in an individual who had previously been treated for prostate cancer. The invention further includes methods treating an individual with benign pro static hyperplasia (BPH) as well as methods of screening for compounds that inhibit the proliferation of prostate cancer cells. The invention provides for compositions and articles of manufacture containing quercetin in particular formulations, or quercetin with a second compound that also exerts an effect on the androgen receptor.

It was shown herein that quercetin inhibited androgen-stimulated secretion of both prostate-specific antigen (PSA) and hK2. The expression of the androgen receptor was diminished by quercetin. The invention provides a novel aspect of quercetin in that quercetin can attenuate androgen receptor-mediated transactivation of prostate cancer-specific genes in androgen-responsive prostate cancer cells. Thus, the invention provides for methods of preventing or treating prostate cancer using quercetin.

The Androgen Receptor and Prostate Cancer

Androgens play an important role in the proliferation, differentiation, maintenance, and function of the prostate. The androgen receptor is the essential mediator for androgen action and is a ligand-dependent transcription factor belonging to the nuclear steroid hormone receptor superfamily. Androgens can enhance androgen receptor protein levels by increasing the half-life, as well as by stimulating the phosphorylation of the androgen receptor. Phosphorylation may affect numerous characteristics of nuclear receptors including ligand binding, nuclear translocation, dimerization, DNA binding, and protein—protein interactions.

Evidence shows that androgens are also involved in the development and progression of prostate cancer. Therefore, the androgen receptor also plays a critical role in the development of prostate cancer, in part due to overstimulation of the receptor by androgens. Prostate cancer also has been attributed to altered transactivation activities of the receptor or to mutations in the androgen receptor that, for example, enable the receptor to respond to non-androgen steroids. The androgen receptor can be expressed in all stages of prostate cancer, and at least one-third of advanced prostate cancers contain amplified androgen receptor genes.

The utilization of androgen deprivation as a treatment for advanced prostate cancer was first demonstrated in 1941 and has become a standard treatment. Based on the morbidity associated with ablation of the adrenal glands, castration alone was the gold standard until the 1980s, when anti-androgen agents, including cyproterone acetate, megestrol acetate, and flutamide, were developed to compete with androgen for binding to the androgen receptor. Many new classes of drugs that interfere with androgen production and function have been identified.

In spite of the apparent regression of tumors by hormone therapy, however, prostate cancer often recurs within 3 years and becomes hormone refractory with a potentially fatal outcome. Many molecular mechanisms have been postulated to be responsible for the development of recurrent hormone-refractory tumors with most involving alterations in the function of the androgen receptor and its complex signaling pathways. The androgen receptor can be activated by a number of growth factors or cytokines in the absence of androgens or by low levels of androgens or other non-androgenic steroid hormones after hormone therapy. That the majority of hormone-refractory cancers still express the androgen-responsive prostate-specific antigen PSA is a protein secreted by the epithelial cells of the prostate gland, including prostate cancer cells. An abnormally high level of PSA is indicative of abnormal prostate cells. (PSA) gene indicates that the androgen receptor signaling pathway is functional.

Nucleic acid sequences encoding androgen receptors have been cloned and sequenced from numerous organisms. Representative organisms and GenBank accession numbers for androgen receptor sequences therefrom include the following: frog (*Xenopus laevis,* U67129), mouse (*Mus musculus,* 109558), rat (*Rattus norvegicus,* 292896), human (*Homo sapiens,* 105325), rabbit (*Oryctolagus cuniculus,* 577829), cow (*Bos taurus,* Z75313, Z75314, Z75315), canary (*Serinus canaria,* 414734), and whiptail lizard (*Cnemidophous uniparens,* 1195596). Additionally, Cancer Genetics Web (www.cancer-genetics.org) contains database entries for wild-type and mutant androgen receptor sequences.

Quercetin

Quercetin is a naturally occurring, water-soluble bioflavonoid found in red wine, red apples, onions, green and black tea, leafy green vegetables, and beans. Quercetin can act as an antihistamine and has demonstrated anti-inflammatory activity. Quercetin also can exhibit antioxidant effects that protect LDL cholesterol from becoming damaged and can inhibit carcinogen activation as well as cellular damage due to radical reactions. Furthermore, quercetin is a potent natural reverse transcriptase inhibitor, and has been shown to have antiviral activity against HIV, herpes simplex, poliovirus and respiratory syncytial virus. In addition to those already discussed, quercetin has been used in connection with the following conditions: capillary fragility, asthma, atherosclerosis, cataracts, diabetes, edema, gout, hay fever, high cholesterol, peptic ulcer and retinopathy.

At relatively high concentrations, quercetin inhibits the proliferation of malignant cells by arresting the cell cycle in the late GI phase and by causing apoptosis. Quercetin also blocks signal transduction pathways by inhibiting protein tyrosine kinase, 1-phosphatidylinositol 4-kinase, and 1-phosphatidylinositol 4-phosphate 5-kinase resulting in a reduction of inositol 1,4,5-trisphosphate concentration. Quercetin can down-regulate the expression of oncogenes, e.g., c-myc and ki-ras, and induce wild-type p53. In addition, quercetin can down-regulate the estrogen receptor in an estrogen-sensitive breast cancer cell line, MCF-7. Further, quercetin blocks an enzyme that leads to the accumulation of sorbitol, which has been linked to nerve, eye, and kidney damage in those with diabetes.

Methods of Monitoring and Inhibiting the Proliferation of Prostate Cancer Cells

The invention provides for methods of monitoring the proliferation of prostate cancer cells. According to the methods of the invention, the proliferation of prostate cancer cells can be monitored by contacting those cells with quercetin and then determining the level of expression of the androgen receptor using conventional methods (e.g., methods described herein). A decrease in expression is indicative of an inhibitory effect by quercetin on the proliferation of the prostate cancer cells. Proliferation of prostate cancer cells as used herein refers to an increase in the number of prostate cancer cells (in vitro or in vivo) over a given period of time (e.g., hours, days, weeks, or months). It is noted that the number of prostate cancer cells is not static and reflects both the number of cells undergoing cell division and the number of cells dying (e.g., by apoptosis). An inhibition of the proliferation of prostate cancer cells can be defined as a decrease in the rate of increase in prostate cancer cell number, a complete loss of prostate cancer cells, or any variation therebetween. With respect to tumors, a decrease in the size of a tumor can be an indication of an inhibition of proliferation.

Prostate cancer cells that can be maintained in culture and are useful in the invention include without limitation LNCaP cells and LAPC-4 cells. The LNCaP cell line is an established androgen-responsive prostate cancer cell line obtained from a lymph node metastasis of a prostate cancer patient. LNCaP cells express the androgen receptor and a number of androgen-inducible genes such as PSA, human glandular kallikrein (hK2), NKX3.1 and ornithine decarboxylase (ODC). The gene encoding the androgen receptor in the LNCaP cell line contains a mutation in its ligand binding domain, but otherwise is functional. LAPC-4 cells, another androgen responsive prostate cancer cell line suitable for use in the invention, expresses a wild-type androgen receptor. LAPC-4 cells additionally express PSA and hK2, which are up-regulated in the LAPC-4 cells by androgens. Other prostate cancer cell lines are available and include PC-3 and DU145.

The invention further provides for methods of treating an individual with prostate cancer or at risk of developing prostate cancer. An individual is first identified as having prostate cancer or being at risk for developing prostate cancer and then administered an effective dose of quercetin. The expression of the androgen receptor can be monitored in the individual to evaluate the effects of quercetin on prostate cancer cells. Generally, an inhibition of the expression of the androgen receptor by quercetin inhibits the proliferation of prostate cancer cells, thereby treating the individual.

Prostate cancer cells can be identified using several criteria. Prostate cancer cells in culture (e.g., LNCaP cells) can be characterized by the response of such cells to androgens or androgenic agonists or antagonists. Molecular markers, such as increased or decreased expression of androgen-regulated genes or genes involved in prostate cancer (e.g., PSA, hk2, c-jun, ODC, and NKX3.1) also can be used to characterize prostate cancer cells in culture. Prostate cancer in vivo can be identified by a digital rectal examination of a patient, or by imaging or scanning techniques (e.g., magnetic resonance imaging (MRI), or prostascint scans). In addition, the degree of cellular differentiation can be evaluated in prostate cancer cells from an individual, typically removed via a biopsy of prostate tissue, using a Gleason score. Further, there are several commercially available diagnostic tests for PSA and PSA-11 (e.g., Roche Diagnostics Inc., Indianapolis, Ind.) to screen individuals for prostate cancer and to monitor individuals undergoing treatment for prostate cancer. Prostate cancer can be staged, for example, using a Partin Table and/or a Partin II Table (see Partin et al., 1994, *Urology,* 43:649–59 and http://www.theraseed.com/gloss.html for more information).

For the purpose of this invention, quercetin can be administered orally, transdermally, intravenously, intraperitoneally, or by implantation. The route of administration typically depends on a variety of factors, such as treatment environment and therapeutic goals. Administration of quercetin can be on a continuous or an intermittent basis. In addition, preparations for administration of quercetin can be suitably formulated to give controlled release of the compound. Preparations for intravenous and intraperitoneal administration can include sterile aqueous or non-aqueous solutions, suspensions, and emulsions. Examples of non-aqueous solvents include, without limitation, propylene glycol, polyethylene glycol, vegetable oils, and injectable organic esters. Aqueous carriers include, without limitation, water, as well as alcohol, saline, and buffered solutions. Other additives such as, for example, antimicrobials, antioxidants, chelating agents, inert gases, steroids, anti-inflammatory agents, immunosuppressants, vasodilators, vasoconstrictors, and the like may also be present.

Tablets or capsules for oral administration can be prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Tablets can be coated by methods known in the art. Liquid preparations for oral administration can take the form of, for example, solutions, syrups or suspension, or they can be presented as a dry product for constitution with saline or other suitable liquid vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl- or propyl-p-hydroxybenzoates or sorbic acid). The preparations can also contain buffer salts, flavoring, coloring and sweetening agents as appropriate.

Preparations for transdermal administration are known in the art. Such transdermal preparations can be in the form of a scrotum patch or a patch for application on the back, abdomen, thighs or buttocks. A transdermal patch typically includes a soft flexible backing (e.g., polyester or polyester/ethylene-vinyl acetate copolymer), a reservoir (in some cases, the compound or composition, e.g., quercetin, can be deposited as a film on the ethylene-vinyl acetate copolymer or can be combined with, for example, alcohol and a gelling agent such as hydroxypropyl cellulose), and an adhesive backing made out of, for example, polyisobutylene and colloidal silicon dioxide (usually with a removable liner (e.g., silicone-coated polyester, or fluorocarbon diacrylate) to protect the adhesive until the patch is applied). A transdermal patch also can contain a formulation (e.g., polyisobutylene adhesive) to control the rate of release of the compound or composition.

Implantable devices are known in the art and can be in the form of a pellet or a seed containing or coated with a compound or composition, e.g., quercetin. A pellet or seed can be a metal alloy (e.g., cobalt, or palladium) or an inert plastic or other substance. A device for implantation in or near the prostate can be delivered using a delivery catheter (similar to brachytherapy) and can be deposited in or near the prostate transperineally, transrectally, or transurethrally. A transrectal ultrasound can be used in conjunction with implantation to visualize and image the prostate and the positioning of the implantable device.

According to the invention, an effective dose of quercetin is an amount that inhibits the expression of the androgen receptor, thereby inhibiting the proliferation of prostate cancer cells. Inhibition of the expression of the androgen receptor and the subsequent inhibition of the proliferation of prostate cancer cells can be determined using methods and assays described herein. It is anticipated that an effective dose of quercetin is from about 50 mg of quercetin per kg weight of the individual (mg/kg) to about 1000 mg/kg. Toxicity and therapeutic efficacy of different doses of quercetin can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio of $LD_{50}/ED_{50}$. Doses of quercetin that exhibit high therapeutic indeces are preferred. An effective dose of quercetin can be delivered in a single dose or as multiple doses over a period of time. After quercetin was administered at dose levels that delivered approximately 40 to 1900 mg/kg/day to male and female rats, there were no treatment related effects on survival and no treatment related clinical signs of toxicity.

Expression of a gene encoding an androgen receptor in prostate cancer cells can be examined in the presence and absence of a compound using Northern blot analysis (to evaluate transcription) and/or Western blot analysis (to evaluate translation). Techniques to isolate RNAs and proteins from cells as well as methods of separation (e.g., electrophoretically) are well known and routine in the art. Androgen receptor mRNA can be detected by hybridization with a labeled oligonucleotide probe that is complementary to a portion of the androgen receptor transcript. Androgen receptor proteins can be detected by contacting proteins from a cell with a labeled agent that selectively binds to the androgen receptor protein. Conditions for allowing and detecting hybridization of nucleic acids or binding of antibodies to proteins are well known in the art. Antibodies that have binding affinity to androgen receptor proteins are commercially available (e.g., from Research Diagnostics Inc. (Flanders, N.J.) and Alpha Diagnostic International (San Antonio, Tex.)). The term "label", with regard to an oligonucleotide probe or an antibody is intended to encompass direct labeling of the oligonucleotide or antibody by coupling a detectable substance to the oligonucleotide or antibody, as well as indirect labeling of the oligonucleotide or antibody by reactivity with a detectable substance. Examples of labels and detectable substances are well known in the art. Additional methods to detect androgen receptor mRNA (e.g., RT-PCR or dot blots) or protein (e.g., immunoassays or chromatography) are well known and also practiced routinely in the art.

In addition, the invention provides methods of reducing the risk of recurrence of prostate cancer in an individual that previously had undergone treatment for prostate cancer. Such methods include administering an effective dose of quercetin to the individual such that the expression of the androgen receptor is inhibited. Inhibiting the expression of the androgen receptor inhibits the proliferation, and therefore the recurrence, of prostate cancer cells. Treatments for prostate cancer that an individual might undergo include hormone therapy, chemotherapy, radiation therapy and, oftentimes, a prostatectomy, in which part of all of the prostate gland is removed. A radical prostatectomy includes removal of the entire prostate as well as the seminal vesicles. Due to a high incidence of prostate cancer recurring, even following such treatments (including a radical prostatectomy), methods of the invention provide for administration of quercetin during or following such treatments. Administration of quercetin may be particularly useful following a radical prostatectomy.

The invention additionally provides for a method of treating an individual with benign prostatic hyperplasia (BPH). Individuals with BPH may present with prostatitis and/or difficulty urinating, and an enlarged prostate due to BPH is typically palpable during a digital rectal exam. Methods of the invention include identifying an individual with BPH, and administering a dose of quercetin or a derivative thereof to said individual effective to inhibit the expression of an androgen receptor. Such an inhibition of the androgen receptor's expression reduces the androgen receptor-mediated growth response and thereby treats the individual with BPH.

Methods of Screening Compounds

The invention provides for methods of screening for compounds that inhibit the proliferation of prostate cancer cells by decreasing the expression of the androgen receptor. Screening methods are one of the fundamental tools used in molecular biology for rapid and efficient evaluation of compounds. Screening methods of the invention include contacting prostate cancer cells with a compound under conditions and for a time sufficient to allow the compound to enter the cell, and determining the expression of the androgen receptor. Generally, decreased expression of the androgen receptor in cells compared to cells not contacted with the compound indicates a compound that inhibits the proliferation of prostate cancer cells. Such compounds can be evaluated using prostate cancer cells in culture, such as LNCaP or LAPC-4 cells, or can be evaluated using a cell-free system.

Methods of determining the level of expression of the androgen receptor are described above. The transactivating ability of the androgen receptor can be examined by evaluating the expression of genes whose transcription is regulated by androgen receptor binding. Such genes include PSA, h2k, NKX3.1, and ODC. The amount of transcript and/or protein of such genes in the presence and absence of the compound can be readily determined using art-routine methods such as those described herein. Alternatively, prostate cancer cells in culture can be made transgenic for one or more androgen-regulated genes and the expression of such transgenes can be evaluated in the presence and absence of a compound.

The ability of the androgen receptor to translocate to the nucleus also can be evaluated in the presence and absence of a compound to determine if the compound inhibits the nuclear localization of the androgen receptor. Nuclei are typically isolated using an appropriate gradient such as a sucrose gradient, a percol gradient, or the like. The nuclei can be lysed (for example, by exposure to sonication, or ultrasound waves) and androgen receptor protein can be detected using routine methods such as Western blotting. Nuclear translocation also can be examined using, for example, immunocytochemistry to identify androgen receptor protein in the nucleus and/or outside of the nucleus.

In addition, the amount of c-jun protein can be evaluated as an indicator of androgen receptor activity. When overexpressed, c-jun has been shown to inhibit the expression of the androgen receptor. c-jun is a partner with c-fos in the transcription factor AP-1. Increased evidence suggests that the function of the androgen receptor may be affected by an interaction with AP-1.

Compositions and Articles of Manufacture

The invention provides compositions that include quercetin or a derivative thereof and at least one other compound selected for its particular mechanism of action on the androgen receptor. The mechanism of action exerted by the other compound(s) can be one or more of the following: inhibition of the expression of a gene encoding an androgen receptor; inhibition of the nuclear localization of an androgen receptor; or inhibition of the expression of an androgen receptor. Representative compounds exhibiting such mechanisms of action include the following: POH, resveratrol, and omega-3 fatty acids (transactivating ability); silymarin (nuclear localization); flufenamic acid, and tea polyphenols (e.g., (−)-epigallocatechin gallate (EGCG)) (expression); and numerous anti-androgen compounds (e.g., bicalutamide, flutamide, nilutamide, or cyproterone).

Compositions containing quercetin can be formulated for delivery to the prostate. In one aspect, quercetin is formulated for transdermal delivery to the prostate. In another aspect, compositions containing quercetin can be formulated for implantation in or near the prostate. Delivery of compositions containing quercetin directly to the prostate of an individual inhibits the expression of the androgen receptor. Formulations for administration of quercetin described above and apply as well to the disclosed compositions containing quercetin.

A composition containing quercetin can be in any form provided the composition can be administered to an individual in an amount and for a duration effective to inhibit the expression of the androgen receptor gene, thereby inhibiting the proliferation of prostate cancer cells. Pharmaceutically acceptable carriers include solvents, dispersion media, coatings, antibacterial and anti-fungal agents, isotonic and absorption delaying agents and the like, appropriate to specific routes of administration.

Quercetin compositions of the invention that are effective for inhibiting expression of the androgen receptor as described herein can be combined with packaging material and sold as a kit (i.e., an article of manufacture). Components and methods for producing articles of manufactures are well known. In addition to a composition containing articles of manufacture can include oligonucleotide probes, antibodies, and/or other useful agents for determining the expression of the androgen receptor. Instructions describing how the composition can be used for inhibiting the expression of the androgen receptor to thereby inhibit the proliferation of prostate cancer cells can be included in such kits.

In accordance with the present invention, there may be employed conventional molecular biology, microbiology, biochemical and recombinant DNA techniques within the skill of the art. Such techniques are explained fully in the literature. The invention will be further described in the following examples, which do not limit the scope of the invention described in the claims.

EXAMPLES

Example 1

Cell Cultures and Treatments

The human prostate cancer cell line LNCaP was obtained from The American Type Culture Collection (ATCC, Manassas, Va.). Another human prostate cancer cell line, LAPC-4, was a gift from Dr. Charles Sawyers (University of California at Los Angeles, Los Angeles, Calif.). Both cell lines were propagated in 24-well, 60 or 100 mm culture dishes at the desired density in RPMI 1640 (Mediatech, Herndon, Va.) supplemented with 5% fetal calf serum (FCS) (Biofluids, Rockville, Md.) at 37° C. and 5% $CO_2$ until reaching 50–70% confluence. The cells were treated with quercetin at indicated concentrations with or without 1 nM mibolerone (Mib) (New England Nuclear, Boston, Mass.). Mib is a synthetic androgen that is not metabolized in cell culture. Quercetin was purchased from Sigma (St. Louis, Mo.) and dissolved in DMSO.

Example 2

Western Blot Analysis

LNCaP or LAPC-4 cells were plated in 10 cm dishes at $9\times10^5$ cells per dish in RPMI 1640 and 5% FCS. After 48 hrs, the cells were treated with 1 nM Mib and varying concentrations of quercetin. Cells were harvested at designated times, and the whole cell lysate was prepared according to manufacturer's instructions (Santa Cruz, Santa Cruz, Calif.). Nuclear extraction was performed using the protocol described by Andrews et al. (1991, Nuclic Acids Res., 19:2499). Protein levels were measured with a BioRad DC protein assay (BioRad, Hercules, Calif.). Protein samples (20 µg) were loaded into precast 4–12% NuPage gels (Novex, San Diego, Calif.), run with MOPS buffer, and transferred onto a nitrocellulose membrane (BioRad) according to the manufacturer's instructions. A Ponceau S staining was performed for total protein staining and visualized with a digital camera. The membranes were blocked overnight at 4° C. in TBST (20 mM Tris-HCl (pH 8.0), 137 mM NaCl, and 0.1% Tween 20) and 5% dry milk. The membranes were washed 3 times for ten min each with TBST. Primary antibody for the androgen receptor (1:2,000 dilution) (Pharmingen, San Diego, Calif.), Sp1 (1:2,000 dilution) (Santa Cruz) or heat shock protein70 (Hsp70) (1:1,000 diultion) (StressGene Biotechnologies, Victoria, B.C.) was incubated at room temperature for 1 hr. The membranes were washed 3 times for ten min each with TBST. Anti-mouse horseradish peroxidase (HRP) secondary antibody (Amersham, Piscataway, N.J.) used at a 1:10,000 dilution was also incubated for 1 hr at room temperature. The membranes were washed again and Renaissance chemiluminescence (New England Nuclear, Boston, Mass.) was used according to the manufacturer's instructions.

Example 3

PSA and hK2 Protein Expression

LNCaP cells were seeded at $2\times10^4$ cells per well in 24 well plates. After two days they were treated with varying amounts of quercetin with or without 1 nM Mib. After a 5 day incubation, the spent media were harvested, and the levels of PSA and hK2 quantified by an immunometric assay as described previously (Hsieh et al., 1997, Cancer Res., 57:2651–6). MTS assays were performed (Promega, Madison, Wis.) as per the manufacturer's instructions. The protein levels of PSA and hK2 were normalized by cell density measurements with the MTS assay.

Example 4

Northern Blots

LNCaP cells were treated with the indicated concentrations of quercetin with or without Mib. Cells were harvested 24 hrs later and RNA was isolated by the guanidine isothiocyanate method (Chomczynski et al., 1987, Analyt. Biochem., 162:156–9). Total RNA (15 µg) was run on a denatured gel and transferred onto a nylon membrane according to the GeneScreen protocol (New England Nuclear). cDNAs for PSA, NKX3.1, ODC and the androgen receptor were used as probes and labeled with [$^{32}$P]dCTP by random priming. The hybridizations were performed according to with ExpressHyb Hybridization Solution (Clontech, Palo Alto, Calif.). The films were autoradiographed at –70° C. overnight.

Example 5

Transient Transfection Assays

LNCaP cells were plated in 60 mm dishes until they reached a confluency of 50–70%. Cells were co-transfected with a CMV-β-galactosidase (β-gal) expression vector and a pGL3 vector containing either a 6 Kb PSA promoter or 2 Kb androgen receptor promoter while the parental vector, pGL3, was used as a control (see Ren et al., 2000, Oncogene, 19:1924–32 for a description of the constructs). Transfections were performed using lipofectin (Life Technologies, Grand Island, N.Y.). 24 hrs after the transfection, cells were treated with different concentrations of quercetin with or without Mib and incubated for an additional 24 hrs. Whole cell extracts were prepared and a luciferase assay was performed according to manufacturer's instructions (Promega) for the PSA promoter/luciferase or the androgen receptor promoter/luciferase constructs. β-gal activity was assayed for normalization purposes (Zhang et al., 1999, Endocrin., 140:1665–71). Each transfection was performed three times and standard deviations were calculated.

Example 6

The Effect of Quercetin on the Androgen Receptor

Figure 1B:
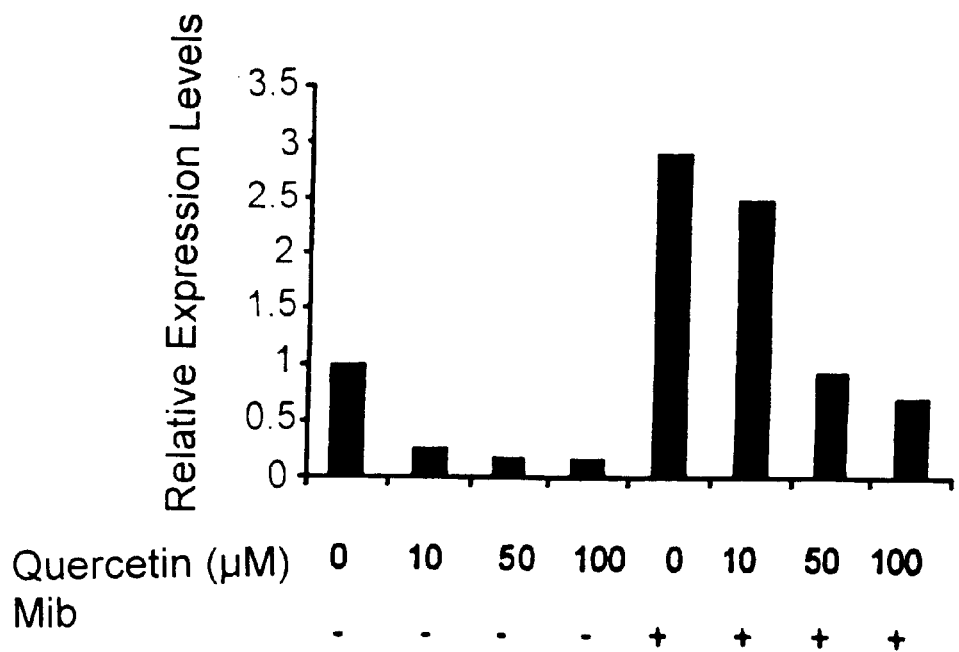

To determine whether the androgen receptor protein levels were changed in the presence of quercetin, Western blots were performed. FIG. 1A shows that the androgen receptor protein levels are decreased in a dose-dependent manner in the presence of quercetin with or without Mib. Since the androgen receptor is a nuclear protein, nuclear extracts were prepared for Western blot. In FIG. 1B, nuclear androgen receptor protein levels were decreased by treatment with quercetin. Transcription factor Sp1 and sp70 were not affected by quercetin treatment.

Figure 1C:
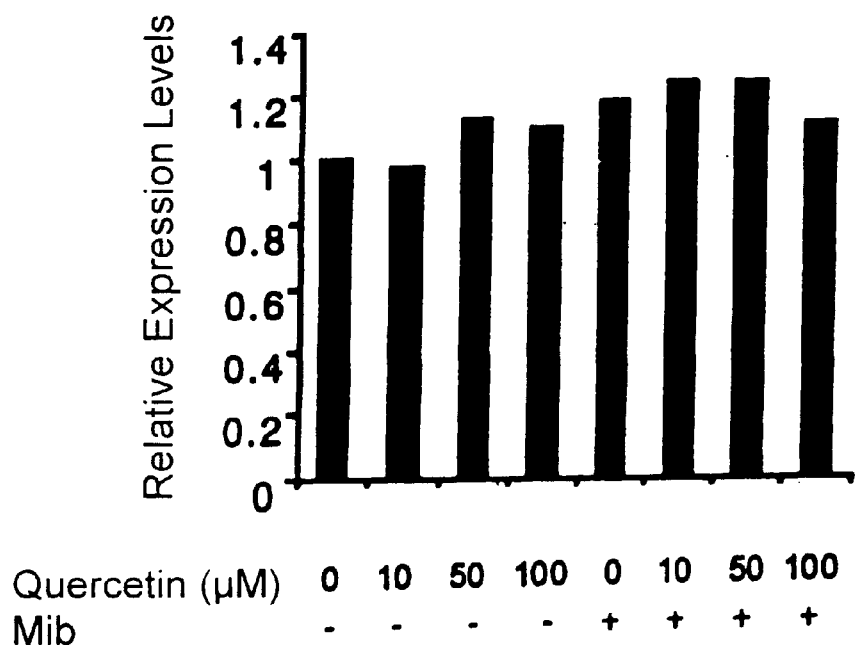
Figure 1D:
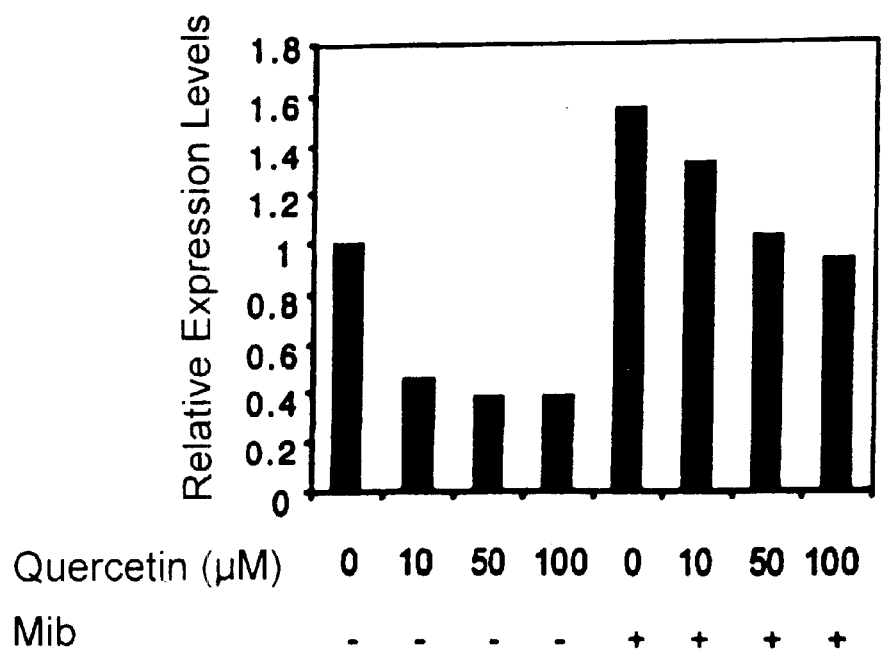
Figure 2A:
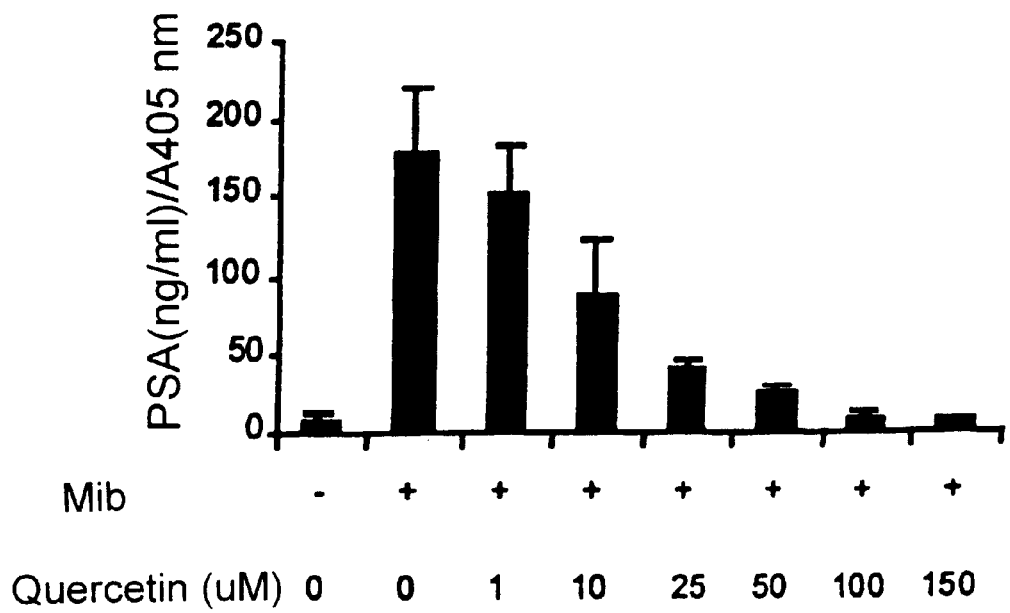
FIG. 2 shows that quercetin inhibits the secretion of PSA (FIGS. 2A and 2C) and hK2 (FIGS. 2B and 2D) in LNCaP and LAPC-4 cells, respectively.
Figure 2B:
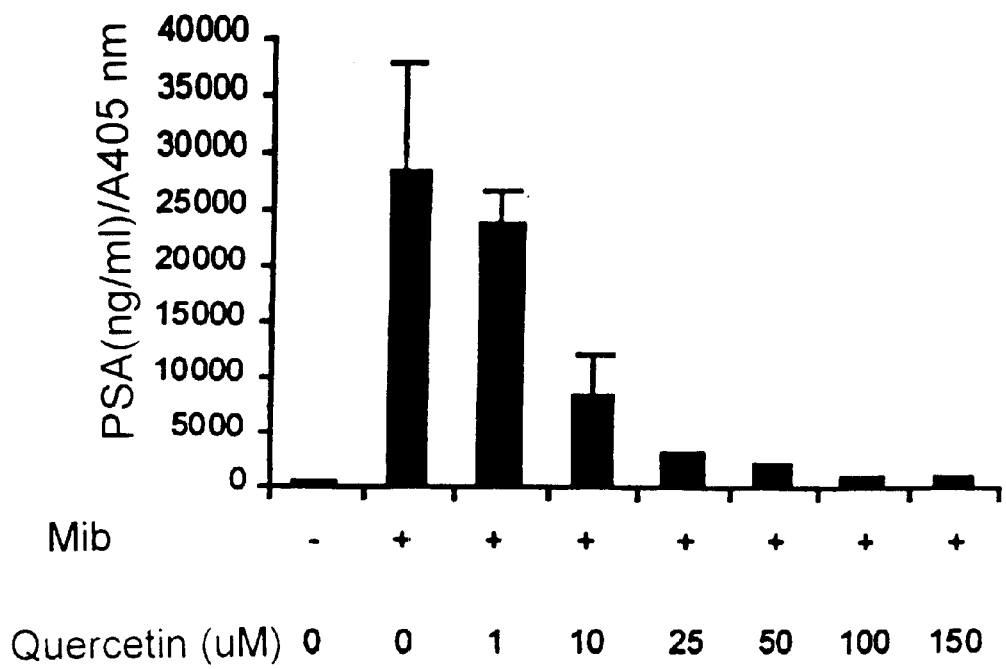
Figure 2C:
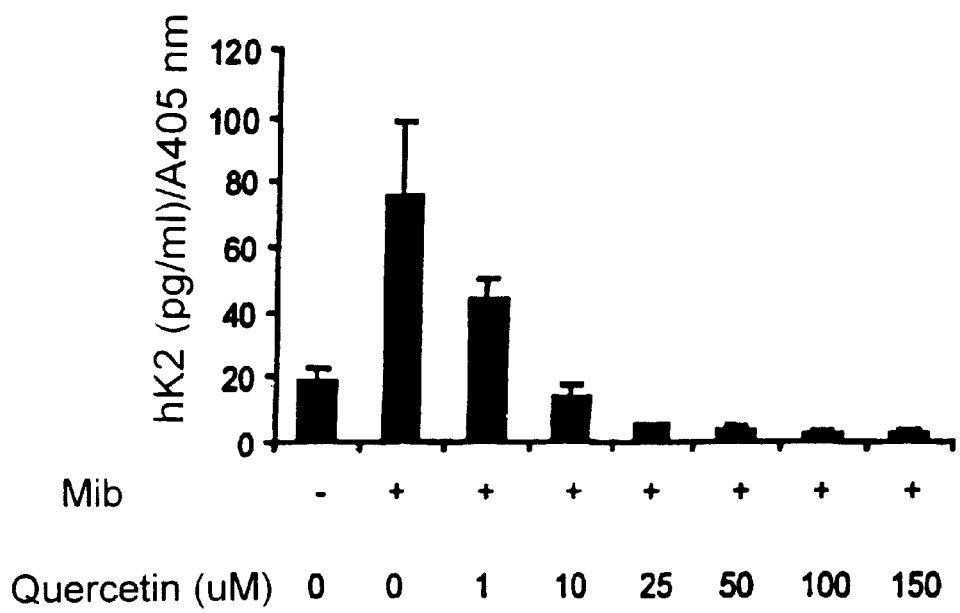
Figure 2D:
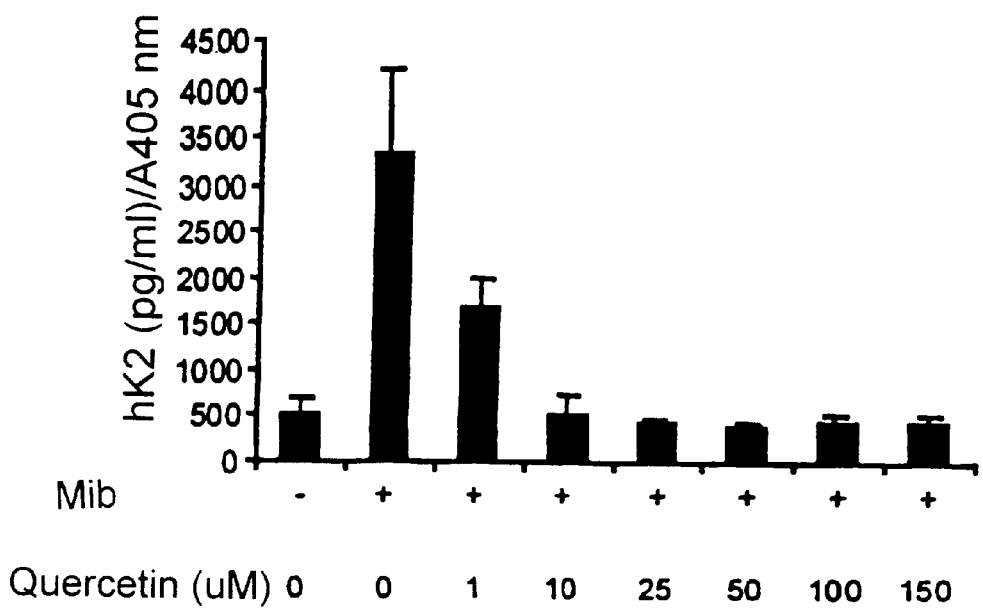

The gene encoding the androgen receptor in the LNCaP cell line contains a mutation in the portion of the sequence encoding its ligand-binding domain, but otherwise is functional. Another androgen responsive prostate cancer cell line, LAPC-4, expressing a wild type androgen receptor, was used to demonstrate that the effect of quercetin on the expression of the androgen receptor is not due to the mutation. Indeed, a similar effect on the androgen receptor by quercetin was found in LAPC-4 cells (FIG. 1D). FIG. 1C shows the expression of Sp1 in the presence and absence of quercetin in whole cell extracts of LNCaP cells.

Example 7

Quercetin Inhibits PSA and hK2 Expression in LNCaP Cells

In order to ascertain if quercetin can actually block androgen action, the androgen-dependent expression of PSA and hK2 was measured. Both PSA and hK2 are prostate specific, androgen-regulated tumor markers. LNCaP or LAPC-4 cells were treated with different concentrations of quercetin with or without Mib for 5 days, and spent media were harvested for assays of total PSA and hK2 proteins. The normalized data in FIG. 2 shows that quercetin inhibits both PSA and hK2 protein levels in a dose-dependent manner in both LNCaP and LAPC-4 cells.

Example 8

Quercetin Inhibits the Expression of Other Classes of Androgen-Regulated Genes In addition to PSA and hK2, NKX3.1 is also a prostate-specific, androgen-regulated gene encoding a homeodomain transcription factor that may play a role in the development and the differentiation of the prostate. Ornithine decarboxylase (ODC) catalyzes the first and rate-limiting step of polyamine synthesis and is regulated in prostate cells by androgen. Northern blot analysis showed quercetin greatly reduced the level of PSA, NKX3.1 and ODC mRNA levels in the presence of androgen.

Example 9

Quercetin Inhibits the PSA Gene at the Transcription Level

Figure 3:
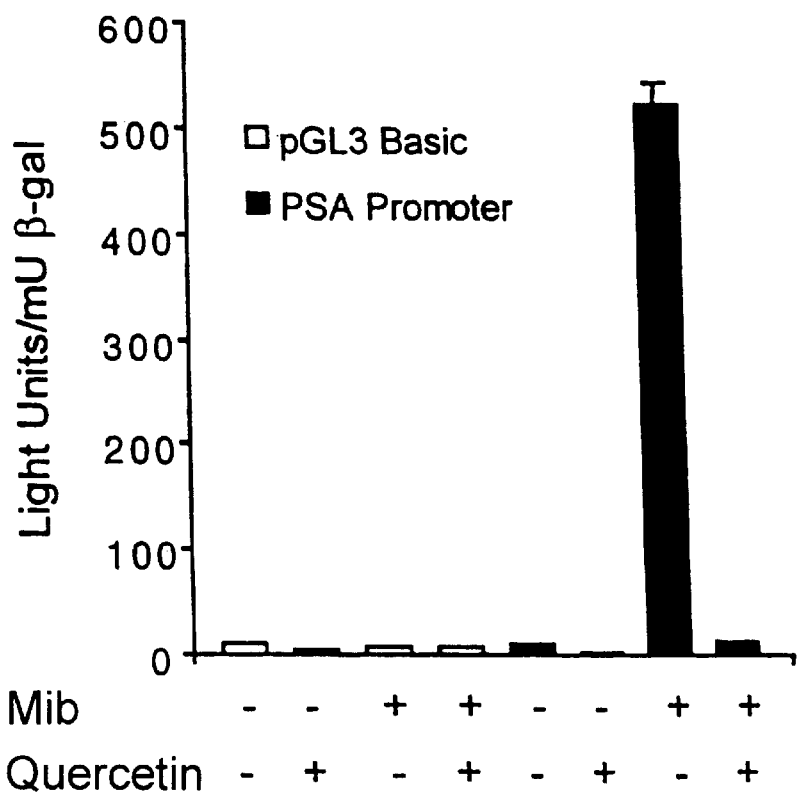
FIG. 3 shows that quercetin inhibits the expression of the PSA gene at the transcription level.

It is well established that the PSA gene is primarily regulated at the transcription level by androgens via interaction of the androgen receptor with androgen responsive elements (AREs) in its promoter. To test whether the inhibitory effect of quercetin on PSA expression occurs at the transcription level, a construct containing a 6 Kb PSA promoter in front of a luciferase reporter gene was transfected into LNCaP cells, which were subsequently grown in the presence or absence of Mib. In Mib-treated cells, the PSA promoter gave a strong androgenic-dependent induction of the luciferase activity, while tranfection with the control vector, pGL3 Basic, showed no induction of luciferase. Treatment with quercetin abolished the androgenic-dependent induction of the 6 Kb PSA promoter ($p<0.01$) (FIG. 3).

Example 10

Figure 4:
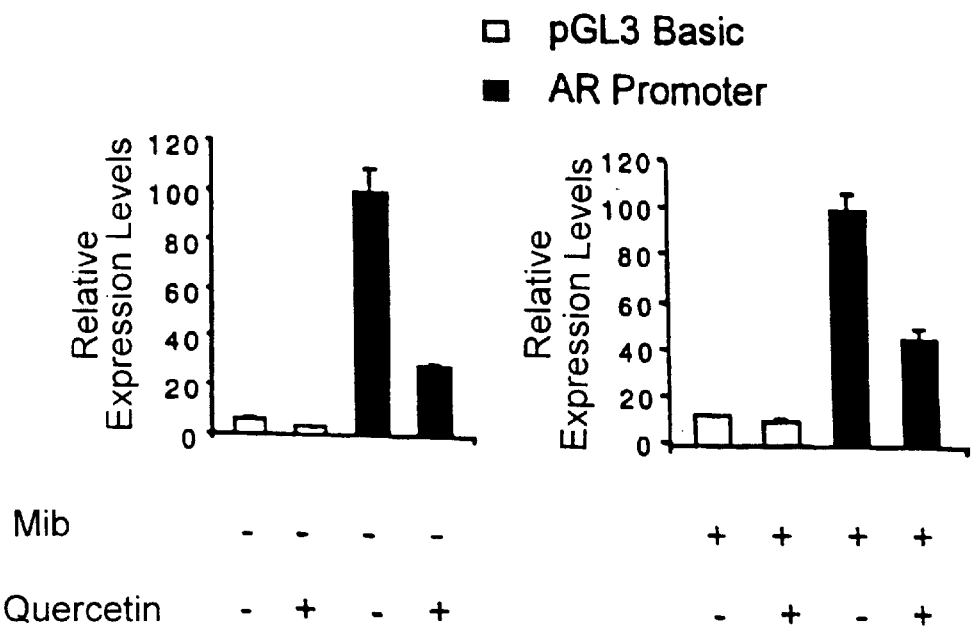
FIG. 4 shows that quercetin inhibits the expression of a 2 Kb androgen receptor promoter expression vector at the transcription level.

Quercetin Inhibits the Expression of the Androgen Receptor Gene at the Transcription Level Northern blot analysis was performed to further examine the mechanism by which quercetin inhibits the expression of the androgen receptor. Androgen receptor mRNA was down-regulated by quercetin treatment. To further ascertain that quercetin can affect the androgen receptor at the transcription level, gene transfer assays were performed with a 2 Kb androgen receptor promoter. FIG. 4 shows that the 2 Kb androgen receptor promoter activity was decreased by quercetin ($p<0.01$) regardless of the presence or absence of androgens.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating an individual with prostate cancer or at risk of developing prostate cancer, comprising the steps of:
   identifying an individual with prostate cancer or at risk of developing prostate cancer;
   administering a dose of quercetin to said individual effective to inhibit expression of a gene encoding an androgen receptor, wherein decreasing androgen receptor expression inhibits the proliferation of prostate cancer cells; and
   monitoring said individual for a dose-dependent reduction in prostate-specific antigen (PSA) levels, wherein said dose-dependent reduction in PSA correlates with a dose-dependent decrease in expression of said gene encoding said androgen receptor.

2. The method of claim 1, further comprising:
   monitoring human glandular kallikrein (hK2) levels in said individual, wherein a reduction in hK2 correlates with a decrease in expression of said gene encoding said androgen receptor.

3. The method of claim 1, further comprising:
   adjusting, if necessary, said dose of quercetin to achieve or maintain said dose-dependent reduction in PSA.

4. A method of treating an individual with prostate cancer or at risk of developing prostate cancer, comprising the steps of:
   identifying an individual with prostate cancer or at risk of developing prostate cancer;
   administering a dose of quercetin to said individual effective to inhibit expression of a gene encoding an androgen receptor, wherein decreasing androgen receptor expression inhibits the proliferation of prostate cancer cells; and
   monitoring human glandular kallikrein (hK2) levels in said individual, wherein a reduction in hK2 correlates with a decrease in expression of said gene encoding said androgen receptor.

5. The method of claim 4, further comprising:
   adjusting, if necessary, said dose of quercetin to achieve or maintain said reduction in hK2.

6. A method of reducing the risk of recurrence of prostate cancer in an individual, wherein said individual previously had been treated for prostate cancer, comprising the steps of:
   administering a dose of quercetin to said individual effective to inhibit expression of a gene encoding an androgen receptor, wherein decreasing androgen receptor expression inhibits the proliferation of prostate cancer cells; and
   monitoring said individual for a dose-dependent reduction in prostate-specific antigen (PSA) levels, wherein said dose-dependent reduction in PSA correlates with a dose-dependent decrease in expression of said gene encoding said androgen receptor.

7. The method of claim 6, further comprising
   monitoring human glandular kallikrein (hK2) levels in said individual, wherein a reduction in hK2 correlates with a decrease in expression of said gene encoding said androgen receptor.

8. The method of claim 6, further comprising:
   adjusting, if necessary, said dose of quercetin to achieve or maintain said dose-dependent reduction in PSA.

9. A method of reducing the risk of recurrence of prostate cancer in an individual, wherein said individual previously had been treated for prostate cancer, comprising the step of:
   administering a dose of quercetin to said individual effective to inhibit expression of a gene encoding an androgen receptor, wherein decreasing androgen receptor expression inhibits the proliferation of prostate cancer cells; and
   monitoring human glandular kallikrein (hK2) levels in said individual, wherein a reduction in hK2 correlates with a decrease in expression of said gene encoding said androgen receptor.

10. The method of claim 9, further comprising:
    adjusting, if necessary, said dose of quercetin to achieve or maintain said reduction in hK2.

11. A method of treating an individual with benign prostatic hyperplasia (BPH) or at risk of developing BPH, comprising the steps of:
    identifying an individual with BPH or at risk of developing BPH;
    administering a dose of quercetin to said individual effective to inhibit expression of a gene encoding an androgen receptor; and monitoring said individual for a dose-dependent reduction in prostate-specific antigen (PSA) levels, wherein said dose-dependent reduction in PSA correlates with a dose-dependent decrease in expression of said gene encoding said androgen receptor.

12. The method of claim 11, further comprising:

monitoring human glandular kallikrein (hK2) levels in said individual, wherein a reduction in hK2 correlates with a decrease in expression of said gene encoding said androgen receptor.

13. The method of claim 11, further comprising:

adjusting, if necessary, said dose of quercetin to achieve or maintain said dose-dependent reduction in PSA.

14. A method of treating an individual with benign prostatic hyperplasia (BPH) or at risk of developing BPH, comprising the steps of:

identifying an individual with BPH or at risk of developing BPH;

administering a dose of quercetin to said individual effective to inhibit expression of a gene encoding an androgen receptor; and monitoring human glandular kallikrein (hK2) levels in said individual, wherein a reduction in hK2 correlates with a decrease in expression of said gene encoding said androgen receptor.

15. The method of claim 14, further comprising:

adjusting, if necessary, said dose of quercetin to achieve or maintain said reduction in hK2.

16. A method of treating an individual with prostate cancer or at risk of developing prostate cancer, comprising the steps of:

identifying an individual with prostate cancer or at risk of developing prostate cancer;

administering a dose of quercetin to said individual effective to inhibit the proliferation of prostate cancer cells; and monitoring said individual for a dose-dependent reduction in prostate-specific antigen (PSA) levels.

17. A method of treating an individual with prostate cancer or at risk of developing prostate cancer, comprising the steps of:

identifying an individual with prostate cancer or at risk of developing prostate cancer;

administering a dose of quercetin to said individual effective to inhibit the proliferation of prostate cancer cells; and monitoring human glandular kallikrein (hK2) levels in said individual.

18. A method of reducing the risk of recurrence of prostate cancer in an individual, wherein said individual previously had been treated for prostate cancer, comprising the steps of:

administering a dose of quercetin to said individual effective to inhibit the proliferation of prostate cancer cells; and monitoring said individual for a dose-dependent reduction in prostate-specific antigen (PSA) levels.

19. A method of reducing the risk of recurrence of prostate cancer in an individual, wherein said individual previously had been treated for prostate cancer, comprising the step of:

administering a dose of quercetin to said individual effective to inhibit the proliferation of prostate cancer cells; and monitoring human glandular kallikrein (hK2) levels in said individual.

20. A method of treating an individual with benign prostatic hyperplasia (BPH) or at risk of developing BPH, comprising the steps of:

identifying an individual with BPH or at risk of developing BPH;

administering a dose of quercetin to said individual effective to inhibit the proliferation of BPH cells; and monitoring said individual for a dose-dependent reduction in prostate-specific antigen (PSA) levels.

21. A method of treating an individual with benign prostatic hyperplasia (BPH) or at risk of developing BPH, comprising the steps of:

identifying an individual with BPH or at risk of developing BPH;

administering a dose of quercetin to said individual effective to inhibit the proliferation of BPH cells; and monitoring human glandular kallikrein (hK2) levels in said individual.

* * * * *

UNITED STATES PATENT AND TRADEMARK OFFICE
CERTIFICATE OF CORRECTION

PATENT NO.   : 6,680,342 B2
DATED        : January 20, 2004
INVENTOR(S)  : Charles Y. F. Young and Nianzeng Xing, PH.D., M.D.

It is certified that error appears in the above-identified patent and that said Letters Patent is hereby corrected as shown below:

<u>Title page,</u>
Item [75], Inventors, please delete "Nianzeng Xing".

Signed and Sealed this

Fourth Day of January, 2005

JON W. DUDAS
*Director of the United States Patent and Trademark Office*